United States Patent [19]

Farr et al.

[11] Patent Number: 4,887,613

[45] Date of Patent: Dec. 19, 1989

[54] CUTTER FOR ATHERECTOMY DEVICE

[75] Inventors: Andrew F. Farr, Spring Valley; Herbert R. Radisch, Jr., San Diego, both of Calif.

[73] Assignee: Interventional Technologies Inc., San Diego, Calif.

[21] Appl. No.: 213,691

[22] Filed: Jun. 30, 1988

Related U.S. Application Data

[63] Continuation-in-part of Ser. No. 123,713, Nov. 23, 1987.

[51] Int. Cl.$^4$ ............................................. A61B 10/00
[52] U.S. Cl. .................................. 606/159; 128/755; 128/757; 128/754
[58] Field of Search ............................ 128/305–313, 128/749, 751–755, 757

[56]  References Cited

U.S. PATENT DOCUMENTS

| | | | |
|---|---|---|---|
| 2,688,329 | 9/1954 | Wallace | 128/349 |
| 3,400,708 | 9/1968 | Scheidt | 128/757 |
| 3,512,519 | 5/1970 | Hall | 128/754 |
| 3,605,721 | 9/1971 | Hallac | 128/754 |
| 3,605,725 | 9/1971 | Bentov | 128/2.05 R |
| 3,618,614 | 11/1971 | Flynn | 128/348 |
| 3,913,568 | 10/1975 | Carpenter | 128/11 |
| 4,195,637 | 4/1980 | Gruntzig et al. | 128/348 |
| 4,307,722 | 12/1981 | Evans | 128/344 |
| 4,441,509 | 4/1984 | Kotsifas et al. | 128/757 |
| 4,545,390 | 10/1985 | Leary | 128/772 |
| 4,571,240 | 2/1986 | Samson et al. | 604/96 |
| 4,582,181 | 4/1986 | Samson | 128/348.1 |
| 4,589,412 | 5/1988 | Kensey | 128/305 |
| 4,690,140 | 9/1987 | Mecca | 128/305 |
| 4,696,667 | 9/1987 | Masch | 604/22 |
| 4,708,147 | 11/1987 | Haaga | 128/305 |
| 4,728,319 | 3/1988 | Masch | 604/22 |
| 4,732,154 | 3/1988 | Shiber | 128/305 |
| 4,754,755 | 7/1988 | Husted | 128/305 |
| 4,757,826 | 7/1988 | Abdulhay | 128/757 |
| 4,765,332 | 8/1988 | Fischell et al. | 128/305 |

Primary Examiner—Max Hindenburg
Attorney, Agent, or Firm—Nydegger & Harshman

[57]  ABSTRACT

A cutter penetrates at its forward end into, and excises, obstructive tissue in a lumen in a living being by providing two spaced external segments of a conical generally hollow portion with cutting surfaces at their edges. The cutter may have a forward portion of restricted dimensions to facilitate the penetration of the cutter into the obstructive tissue. A progressively expanding portion such as a truncated cone extends rearwardly from the portion of restricted dimensions. In this way, the cutter expands the area of excision of the obstructive tissue from the lumen wall at progressive positions rearwardly from the forward end. The obstructive tissue in the lumen at the progressively expanding positions may be excised at the positions of penetration of the obstructive tissue by rotating the cutter manually or by a motor. The cutter may then be moved forwardly to penetrate the obstructive tissue through an additional distance in the lumen. The cutter may also have a hollow portion of substantially constant dimensions, such as a hollow cylinder, at the laterally expanded end. This hollow cylinder is coupled to a torque tube which has strong and resilient properties to follow the contour of the lumen and to communicate a penetrating force to the forward end of the cutter and a torque to the cutter to rotate the cutter. A vacuum may be applied to the cutter through the torque tube to remove fragments of obstructive tissue excised from the lumen.

10 Claims, 3 Drawing Sheets

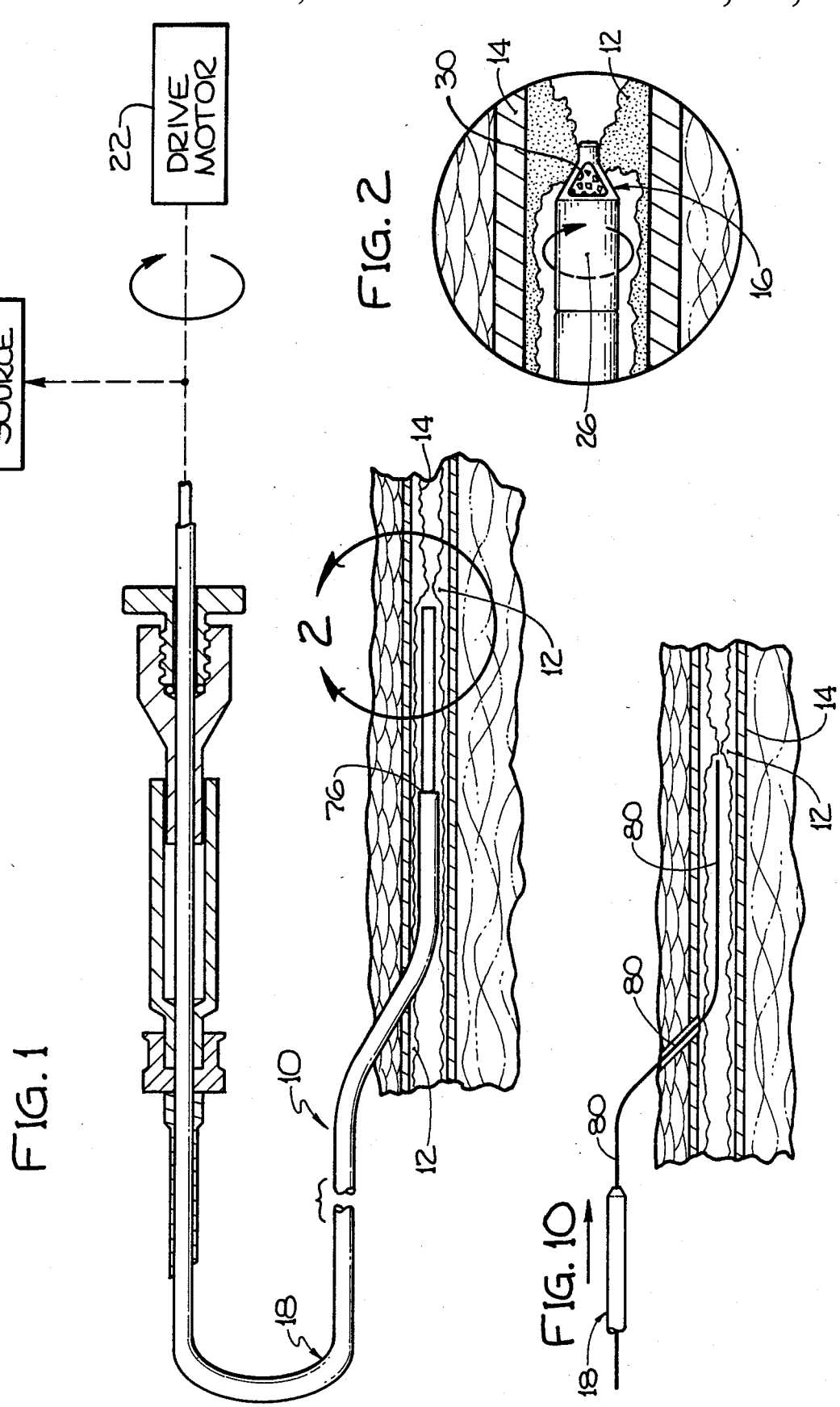

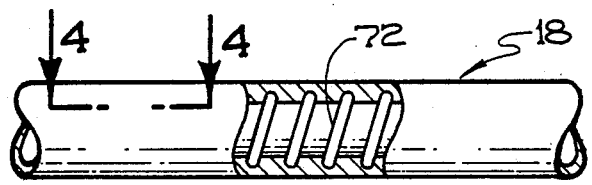
FIG. 3
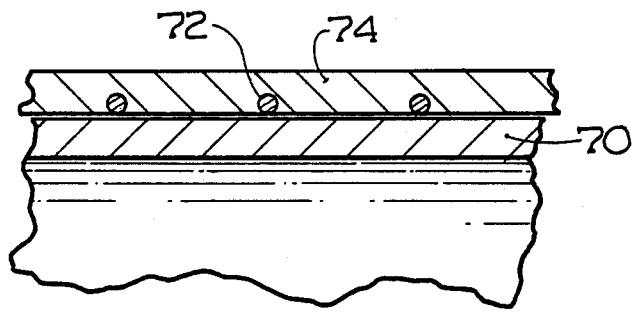
FIG. 4
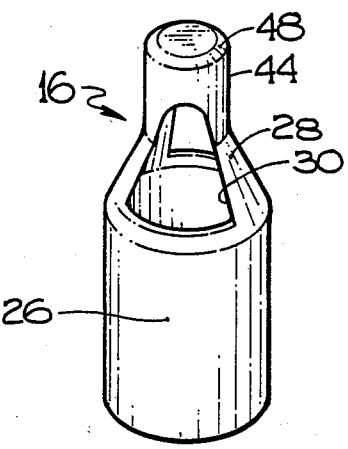
FIG. 5
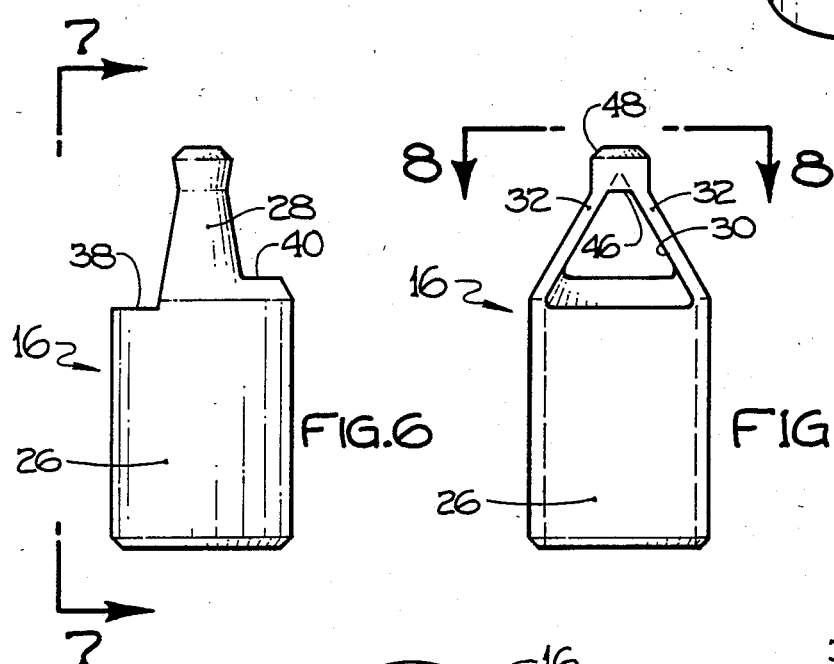
FIG. 6
FIG. 7
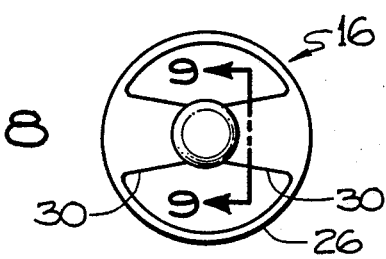
FIG. 8
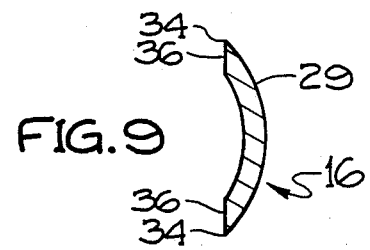
FIG. 9

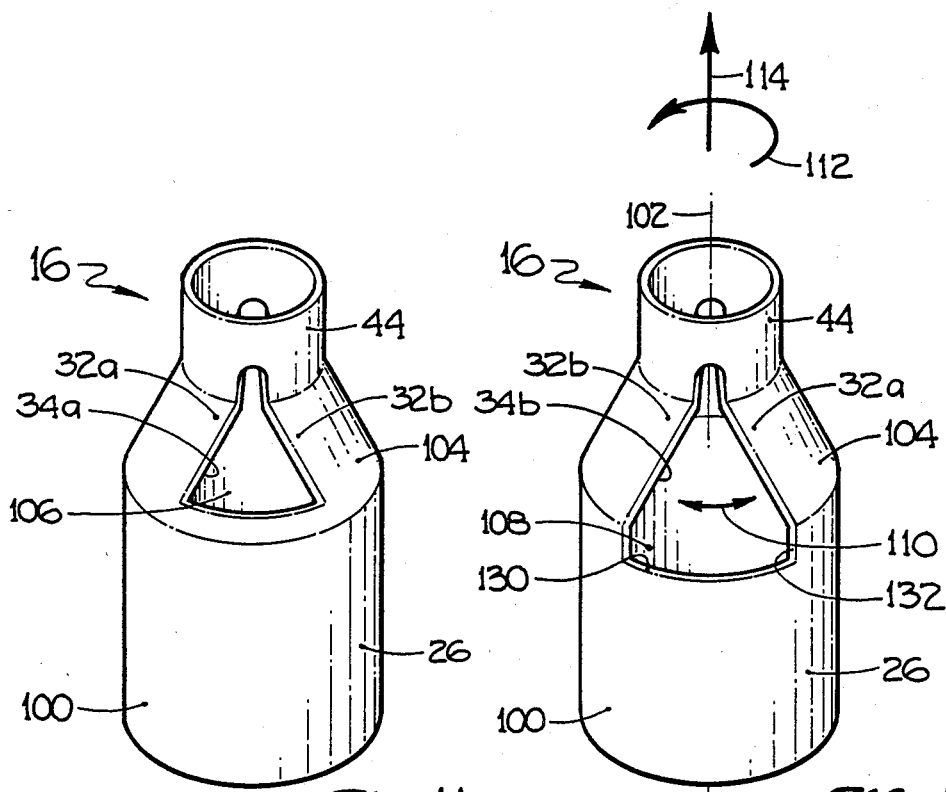
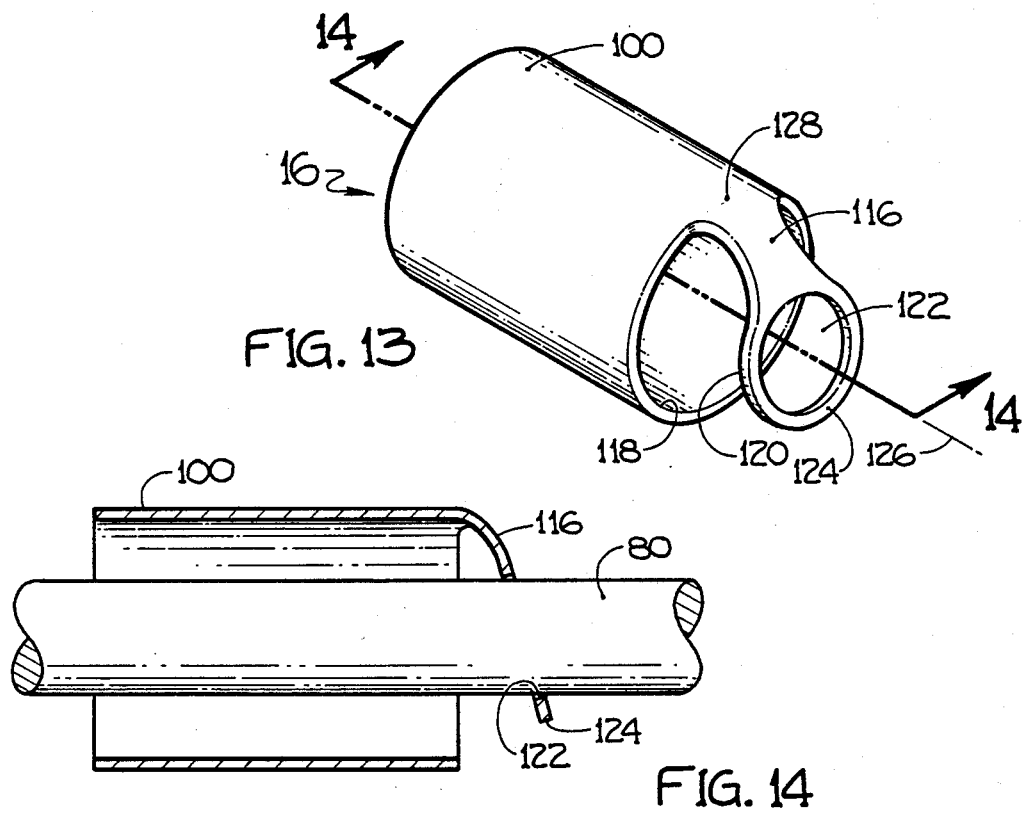

4,887,613

CUTTER FOR ATHERECTOMY DEVICE

BACKGROUND OF THE INVENTION

This application is a continuation-in-part of our prior co-pending application for a "System For, and Method of, Excising Obstructive Tissue from Lumen of Living Beings," Ser. No. 123,713 filed Nov. 23, 1987 still pending.

This invention relates to apparatus for excising obstructive tissue in lumens of living beings. The invention also relates to a cutter for inclusion in such apparatus for excising such obstructive tissue from such lumens even when such obstructive tissue is hard and/or diffuse. The invention also relates to method of forming the cutter and further relates to methods of removing obstructive tissue from the lumen of living beings.

DISCUSSION OF THE PRIOR ART

Heart attacks constitute one of the major sources of incapacitation and/or death to human beings. Such failures have often resulted from blockages in coronary arteries. Such blockages have resulted from the accumulation of plaque in the arterial walls. Such accumulation of plaque has gradually blocked the flow of blood through the arteries to the heart until there is complete stoppage or almost a complete stoppage.

Blockage of arteries other than adjacent to the heart can also cause incapacitation and/or death to human beings. For example, plaque build-up in the arteries of the arms or legs can result in limb amputations; plaque build-up in the arteries of the head and neck can result in strokes; plaque build-up in the arteries of the kidneys can result in hypertension (high blood pressure); and plaque build-up in other peripheral (noncoronary) arteries can result in degradation of the organs which they supply.

Until relatively recently, it has been difficult to diagnose the accumulation of plaque in the arteries of living being. In recent years, however, techniques have been devised for detecting and locating the accumulation of plaque on the arterial walls of living beings. The techniques have become so advanced that probes can be extended through the arteries to progressive positions along the arteries to locate the positions of blockage and to estimate the relative amount of arterial blockage at such progressive positions.

Techniques have been developed for correcting for blockages in the arteries of living beings. One technique often used has been designated as by-pass surgery. In by-pass surgery, the blocked portion of an artery is shunted using a segment of a vessel from another part of the body of the afflicted human being.

By-pass operations represent a considerable danger to the living being undergoing the operation. One reason is that the living being has to be cut open and his heart has to be exposed. The patient also has to undergo anesthesia, the effects of which are often unpredictable. The trauma resulting from the anesthesia and the opening of the body of the living being presents a grave danger to the patient. As a result, by-pass operations should be avoided whenever possible.

Another method has also been developed in recent years to alleviate the blockage of arteries in living beings. This method involves the insertion of a balloon into the artery at a position removed from the blocked position in the artery of the living being. The balloon is moved as by a conduit to the blocked position in the artery. The balloon is then inflated to expand the diameter of the artery to the blocked position. By expanding the diameter of the artery, the opening in the artery at the blocked position is enlarged, thereby alleviating the blockage.

The balloon method has certain inherent disadvantages. It is not desirable to expand the arterial wall at the blocked position because the expansion tends to stretch, and thereby weaken, the arterial wall. Furthermore, the plaque blocking the artery is often quite hard, fibrous, calcified and/or diffuse. This makes it difficult for the balloon to overcome the counterforce exerted by the plaque against the balloon. It has accordingly been difficult to expand the arterial wall against this counterforce. This is particularly true when the plaque is quite thick at the position where the balloon is being inflated.

Since it has been appreciated that the methods discussed in the previous paragraphs, although beneficial, have serious limitations, considerable efforts have been made, and significant sums of money have been expended, to overcome such limitations. Such efforts have not only been devoted to the improvement of present methods and apparatus but also to the development of new methods and apparatus. In spite of such efforts, the methods and apparatus discussed in the previous paragraphs have continued in use.

SUMMARY OF THE INVENTION

This invention provides apparatus for, and a method of, overcoming the disadvantages discussed above. The system and method of this invention provide a torque tube which can be easily and efficiently inserted into the artery and manipulated to the position at which the plaque is blocking the passage of blood in the artery. The apparatus of this invention also includes a cutter which excises plaque from the arterial walls even when the plaque is hard, fibrous, calcified and/or diffuse. The apparatus then removes the plaque fragments efficiently, as by a vacuum, from the blood stream. In this way, any danger is eliminated of having the removed plaque block the artery at a position downstream from that at which the plaque is excised from the material wall. The invention also provides a method of forming the cutter. The invention further provides a method of excising plaque from the aterial walls.

In one embodiment of the invention, a cutter penetrates at its forward end into, and excises, obstructive tissue in a lumen in a living being by providing two spaced external segments of a cylindrical generally hollow portion with cutting surfaces at their edges. The cutter may have a forward portion of restricted dimensions to facilitate the penetration of the cutter into the obstructive tissue.

A progressively expanding portion such as a truncated cone extends rearwardly from the portion of restricted dimensions. In this way, the cutter enlarges the area of excision of the obstructive tissue from the lumen wall at progressive positions rearwardly from the forward end. The obstructive tissue in the lumen at the progressively expanding positions may be excised at the positions of penetration of the obstructive tissue by rotating the cutter manually or by a motor. The cutter may then be moved forwardly to penetrate the obstructive tissue through an additional distance in the lumen.

The cutter may also have a hollow portion of substantially constant dimensions, such as a hollow cylinder, at the laterally expanded end. This hollow cylinder is coupled to a torque tube which has strong and resilient properties to follow the contour of the lumen and to communicate a penetrating force to the forward end of the cutter and a torque to the cutter to rotate the cutter. A vacuum may be applied to the cutter through the torque tube to remove fragments of obstructive tissue excised from the lumen.

The novel features of this invention, as well as the invention itself, both as to its structure and its operation, will be best understood from the accompanying drawings, taken in conjunction with the accompanying description, in which similar reference characters refer to similar parts, and in which:

BRIEF DESCRIPTION OF THE DRAWINGS

In the drawings:

FIG. 1 is a schematic view, partially in section as to the mechanical features and partially in block form as to the electrical features, showing one embodiment of an invention for excising obstructive tissue from the lumen of a living being;

FIG. 2 is an enlarged fragmentary sectional view of a portion of the embodiment in FIG. 1, this portion being encircled by an arrow in FIG. 1 and the arrow being identified by the numeral "2";

FIG. 3 is an enlarged fragmentary view, partially broken to indicate elements in section, of a torque tube included in the embodiment shown in FIGS. 1 and 2;

FIG. 4 is an enlarged fragmentary sectional view taken substantially on the line 4—4 of FIG. 3 and illustrating certain components in the torque tube in further detail;

FIG. 5 is an enlarged perspective view of a cutter included in the embodiment shown in FIGS. 1 and 2;

FIG. 6 is an enlarged elevational view of the cutter shown in FIG. 5;

FIG. 7 is an enlarged sectional view, taken on the line 7—7 of FIG. 6, of the cutter shown in FIGS. 5 and 6 and schematically illustrates additional details of construction of the cutter;

FIG. 8 is an enlarged fragmentary sectional view taken substantially on the line 8—8 of FIG. 7 and illustrates the construction of the cutter at the front end of the cutter;

FIG. 9 is a sectional view of the cutter and is taken substantially on the line 9—9 of FIG. 9;

FIG. 10 is a view schematically illustrating how the cutter and the torque tube are advanced along a guide wire in the lumen to the position where the obstructive tissue to be excised is located;

FIG. 11 is a perspective view of the front of the cutter;

FIG. 12 is a perspective view of the back of the cutter;

FIG. 13 is a perspective view of an alternate embodiment of a cutter; and

FIG. 14 is a cross-sectional view of the cutter as seen along the line 14—14 in FIG. 13.

DESCRIPTION OF THE PREFERRED EMBODIMENTS

In one embodiment of the invention, a system generally indicated at 10 is provided for excising obstructive tissue such as plaque 12 from a lumen such as an artery 14 in a living being such as a human. The system includes a cutter generally indicated at 16, a torque tube generally indicated at 18 and a source 20 of vacuum. The system may also include a motor 22 for rotating the torque tube 18 and the cutter 16 at a relatively low speed to excise the plaque 12 from the artery 14.

The cutter 16 may be made from a suitable material such as a stainless steel. The cutter 16 includes a hollow end portion 26 (FIGS. 5, 6 and 7) having a substantially constant shape such as a cylinder. In one embodiment of the invention, the external diameter of the cylindrical portion 26 may be approximately seventy-two thousandths of an inch (0.072"). The thickness of the portion 26 may be approximately four thousandths of an inch (0.004"). The length of the portion 26 may be approximately one tenth of an inch (0.1"). These dimensions are only illustrative since the cutter 16 may be made in different sizes in accordance with the size of the lumen in which the cutter is received.

An intermediate portion 28 of progressively decreasing dimensions extends from the end portion 26. The intermediate portion 28 may have an external length of approximately five hundredths of an inch (0.05") and may constitute a segment of a truncated cone. The diameter of the intermediate portion 28 at the thin or truncated end of the segmented cone may be approximately twenty-two thousandths of an inch (0.022"). As will be appreciated, these dimensions are also only illustrative.

The intermediate portion 28 is substantially hollow as indicated at 30 in FIGS. 5 and 7. The intermediate portion 28 has a pair of diametrically disposed blades 32 defined by cutting edges 34 (FIG. 9). The cutting edges 34 are preferably quite sharp. The sharpness of the cutting edges 34 is enhanced by a progressive tapering (as indicated at 36), at the lateral ends of the blades 32, of the distance between the external and internal walls defining the thickness of the blades. The maximum thickness of each of the blades 32 may be on the order of one thousandths to two thousandths of an inch (0.001"–0.002"). Each of the blades 32 preferably has external and internal surfaces with annular configurations. The external and internal sufaces of the blades 32 may extend annularly for an angle of approximately fifty degrees (50°) or sixty degrees (60°).

The blades 32 are longer at one end than at the other end. This may be seen by comparing the blades 32 at positions 38 and 40 in FIG. 6. The increased length of the blades 32 at the position 38 results from a cut made in the end portion 26 at a position adjacent the intermediate portion 28. As will be appreciated, the taper in the blades 32 at the side adjacent the position 38 may be more shallow than the taper of the blades at the side adjacent the position 40.

A tip portion 44 extends from the intermediate portion 28. The tip portion 44 has a substantially constant shape adjacent the truncated end of the intermediate portion 28. For example, the tip portion 44 may be cylindrical adjacent the truncated end of the intermediate portion 28. The external diameter of this cylinder may be approximately twenty-three thousandths of an inch (0.023"). The diameter of this cylinder may conform substantially to the width of the blades 32 at the truncated ends of the blades. The opening 30 in the intermediate portion 28 extends partially into the tip portion 44 as indicated at 46 in FIG. 7.

A conical portion 48 extends from the cylindrical portion of the tip portion 44. The diameter of the conical portion 48 at the free end of the conical portion may be approximately sixteen thousandths of an inch (0.016"). The conical portion is open at its forward end as indicated at 49 in FIG. 5. The total length of the tip portion 44 may be approximately fifteen thousandths to twenty thousandths of an inch (0.015"-0.020"). The blades 32 are integrated at their forward ends by the tip portion 44. This imparts strength to the blades 32.

The cutter 16 may be initially formed with (a) a solid end portion having the external configuration of the end portion 26, (b) a solid conical portion having the external configuration of the intermediate portion 28 and (c) a tip portion having the external configuration of the tip portion 44. A cylindrical hole may be formed in the end portion 26 and a cylindrical hole may be formed in the tip portion 44 to form the opening 49. The intermediate portion 28 is then burned as by electrical discharge machining to form the opening 30 (and the extended opening 46) to define the blades 32.

It will be appreciated that the dimensions given above are only by way of example for one embodiment. Actually, applicants have constructed a number of embodiments of different sizes. Each individual embodiment is intended to be operative in a lumen having an opening of an individual size so as to excise obstructive tissue from the lumen.

The basic embodiment of cutter 16 will be still further appreciated with reference to FIG. 11 and FIG. 12. In these figures, it will be seen that cylinder 26 establishes a base 100, and that base 100 is coaxially aligned with cylindrical-shaped tip 44. More specifically, as best described with references to axis 102 in FIG. 12, base 100 is coaxially aligned and distanced from tip 44 along axis 102. Because the diameter of tip 4 is less than the diameter of base 100, the region intermediate tip 44 and base 100 establishes a hollow frustum 104 therebetween. A hole 106 is cut into frustum 104 substantially as shown in FIG. 11 and a hole 108 is cut into frustum 104 diametrically opposite from hole 106 substantially as shown in FIG. 12. With this configuration, holes 106 and 108 in frustum 104 create the substantially straight blades 32a and 32b which connect tip 44 with base 100. FIGS. 11 and 12 also show that hole 108 extends longitudinally farther into base 100 than does hole 106. The result of this difference is that cutting edge 34a of blade 32a is shorter than cutting edge 34b of blade 32b.

FIG. 12 shows that blades 32a and 32b are each inclined to the axis 102 at an angle 110 which is approximately equal to forty-five degrees (45°). It will be appreciated, however, that for the purposes of the present invention angle 110 can range between approximately forty and seventy degrees (40°-70°).

With specific reference to FIG. 12 it will be appreciated that cutter 16 is intended to be rotated about axis 102 in the direction of arrow 112. Further, it is intended that cutter 16 be advanced, as necessary, along axis 102 in the direction of arrow 114. The intention here, of course, is to accomplish the operation generally shown in FIGS. 1 and 2. In accomplishing this operation, cutting edges 34a and 34b are the respective leading edges of blades 32a and 32b. As such, they cut into the obstructive tissue. It happens, however, since edge 32a is shorter than edge 32b, edge 32a makes a smaller cut into the obstructive tissue than will edge 32b. Thus, the side of cutter 16 on which blade 32a is located encounters more resistive tissue. The result of this differential cutting is that cutter 16 tends to deflect off axis 102 away from blade 32a and in the direction of blade 34b. As intended by the present invention, this deflection ensures that the broader sweep of blade 32b is able to cut a channel into the obstructive tissue which has a diameter that is equal to or slightly greater than the diameter of base 100. This is necessary in order for cutter 16 to advance into, rather than getting hung up on the obstructive tissue.

As best seen in FIG. 12, hole 108 extends longitudinally into base 100 to establish a heel 130. It will also be seen in FIG. 12 that the length of edge 132 determines the distance of heel 130 from frustum 104. Importantly, it has been found that the length of edge 132 establishes the extent to which blade 32b will cut into the obstructive tissue. Indeed, it has been determined that the aggressiveness of cutter 16 is directly proportional to the depth of heel 130, as established by the length of edge 132. It will be appreciated by the skilled artisan that this aggressiveness, together with the deflection of cutter 16 as disclosed above, will determine the rate at which obstructive tissue is excised by cutter 16.

It will be appreciated that with the structure herein disclosed for cutter 16 that guide wire 80 can be passed through base 100, frustum 104 and tip 44 in a manner which will allow wire 80 to guide cutter 6 along a predetermined path. Means to rotate cutter 16 for its intened purpose can then be operatively attached to cutter 16.

In the alternate embodiment of cutter 16 shown in FIGS. 13 and 14, base 100 is formed with a curved blade 116 which extends from the forward edge 118 of base 100. The butt 128 of blade 116 may be integral with the forward edge 118 or attached thereto by any means well known in the art. A cutting edge 120 is formed on curved blade 116 which will cut obstructive tissue during the rotation of cutter 16. A hole 122 is formed at the end 124 of curved blade 116 and is positioned with respect to cutter 16 to intersect the longitudinal axis 126 of cutter 16. As best seen in FIG. 14, hole 122 is positioned to surroundingly receive the guide wire 80 therethrough. Also, as best seen in FIG. 14, blade 116 is preferably curved such that the portion of blade 116 wherein hole 122 is formed will lie in a plane that is substantially prependicular to axis 126. With this structure, curved blade 116 can be rotated about wire 80 for cutting obstructive tissue from the lumen into which guide wire 80 has been placed.

The torque tube 18 may include a thin polymeric liner 70 (FIG. 4) made from a suitable material such as a polyamide. However, polyamides or other polymeric materials may also be used for the line 70. In one embodiment, the liner 70 may have a suitable thickness such as approximately five thousandths of an inch (0.005") and may have a suitable inner diameter such as approximately forty-three thousandths of an inch (0.0.43").

A wire 72 made from a suitable material such as tungsten may be wound spirally on the liner 70. Tungsten is desirable because it is strong and resilient and is able to transmit torque, particularly when spirally wound. However, the wire 72 may also be made from other suitable materials such as stainless steel, titanium or polymers. In one embodiment, the wire 72 may have a suitable diameter such as approximately two thousandths of an inch (0.002") and a tension modulus of approximately 350 Kpsi. The wire 72 may be wound on the liner 70 at a suitable angle such as an angle of approximately thirty degrees (30°). It will be appreciated that any resilient member with properties corresponding to those of the wire 72 may be used instead of the wire 72.

A matrix 74 is disposed on the liner 70 and the winding 72 and may be provided with a suitable thickness such as approximately three thousandths of an inch (0.003"). The matrix 74 may be made from a mixture of a urethane and an epoxy. When the mixture is cured and subjected to gamma radiation in the order of 12-18 Mrads, the matrix 74 becomes cross-linked three-dimensionally. The cross-linking binds the matrix 74 to the liner 70 and the winding 72. The cross-linking enhances the properties of the torque tube 18 in providing torque transmission and flexibility. Instead of being made from a mixture of a urethane and an epoxy, the matrix 74 may be made from polymeric composites using glass, boron and/or carbon fibers. The liner 70 and the matrix 74 may be considered as a sheath encasing the wire 72.

It will be appreciated that the dimensions specified above for the torque tube 18 are only illustrative. Actually, torque tubes of different sizes may be used when the cutters have different sizes. It will also be appreciated that the combination of the torque tube 18 and the cutter 16 as described above is preferred. However, other coupling members may be used with the cutter 16 than the torque tube 18. Furthermore, other cutters may be used with the torque tube 18 than the cutter 16.

Before the torque tube 18 and the cutter 16 are inserted into the lumen of the living being, an opening is made percutaneously at a suitable position such as the groin of the living being. A thin resilient guide wire 80 (FIG. 10) is then inserted into a lumen such as an artery 14 through the percutaneous opening and is advanced along the lumen to at least the position where the obstructive tissue such as the plaque 12 is to be excised from the lumen. Actually, the resilient guide wire 80 is generally advanced along the lumen to a position beyond the obstruction. The cutter 16 and the torque tube 18 are then disposed on the guide wire 80 and advanced along the guide wire to the position where the obstructive tissue is to be excised from the lumen. The guide wire 80 may be retained in the lumen to provide a guide for the cutter 16, particularly when the cutter is to be advanced along the lumen.

The torque tube 18 may be disposed within a sleeve 76 (FIG. 1) which is disposed in the artery 14. The sleeve 76 may be made from a suitable material such as a polyamide which may be coated with a suitable material such as a urethane. However, other polymers may be used instead of the polyamide and other coatings may be used instead of urethane. The sleeve 76 is stationary and the torque tube 18 is rotated within the sleeve. Since the torque tube 18 is disposed within the sleeve 76, it does not rub against the artery when it is rotated.

The torque tube 18 is then operated to move the portion 44 of the cutter 16 into the plaque 12. This can be accomplished even though the plaque 12 almost completely blocks the artery and even though the plaque may be hard, fibrous, diffuse and/or calcified. This results from the force localized at the tip portion 44 and particularly from the intermediate portion 28 and the cutting edges 34 on the blades 32 in the intermediate portion. Depending upon the size of the opening remaining in the artery as a result of a partial blockage of the artery by the plaque, at least part of the intermediate portion 28 may also penetrate the plaque 12.

The conical portion 48 of the tip 44 is then forced into the plaque 12. The penetration can then be sometimes enlarged by forcing the intermediate portion 28 into the plaque. This can be accomplished because the force is concentrated substantially only at the blades 32 in the intermediate portion 28 and because the blades are relatively thin. The opening produced by the tip portion 44 can sometimes be enlarged because the distance between the blades 32 in the intermediate portion 28 is progressively increased with progressive distances from the tip portion 44.

The tip portion 44 is advanced (and sometimes at least a portion of the intermediate portion 28) into the plaque 12, while the torque tube 18 and the cutter 16 are rotating. The rotation may be accomplished manually or automatically as by the motor 72. When the motor 22 is used, it may be operated at a relatively low speed such as approximately eight hundred revolutions per minute (800 rpm). By operating the motor 22 at a relatively low speed, the operator is able to control the removal of the plaque 12 from the arterial wall 14.

When the torque tube 18 is rotated either manually or by the motor 22, it transmits the torque to the cutter 16. This results from the spiral winding 72 and the cross-linked matrix 74. The resultant rotation of the cutter 16 causes the blades 32 to excise the plaque 12 from the arterial wall 14. When the plaque 12 is excised from the arterial wall 14, it enters the opening 30 between the blades 32. The plaque 12 entering the opening 30 is in a form of small fragments. The fragments of the plaque 12 are then removed through the torque tube 18 by the vacuum applied by the source 20.

The apparatus described above has certain important advantages. It is able to penetrate the plaque 12, even when the plaque is hard, diffuse, fibrous and/or calcified, by concentrating the applied forces at the tip portion 44. It is then sometimes able to expand this penetration by applying the localized forces to an expanding, but thin, area in the intermediate portion 28. The apparatus then excises the plaque 12 in the penetrated area by rotating the cutter 16 to provide a fragmentation of the plaque by the blades 32.

The application of a vacuum to the excised fragments of the plaque 12 is advantageous. It insures that the fragments of the plaque 12 excised from the arterial wall are removed directly from the body of the living being. This prevents the plaque from being deposited in the lumen of an artery at a downstream position. When the fragments of the plaque 12 are removed by the source 20 from the body of the living being, relatively little blood from the living being is lost.

Because of the increased length of the side 38 of each of the blades 32 relative to the length of the blades on the other side 40, the blades are able to excise the obstructive tissue to the full external diameter of the end portion 26. This provides for an enhanced efficiency in the operation of the cutter 16.

It will be appreciated that the above discussion has been principally confined to the excision of plaque 12 from the arterial walls of a living being. This discussion has been for purposes of explanation. As will be appreciated, the apparatus of this invention can be used for excising any obstructive tissue from lumens of living beings withouut departing from the scope of this invention.

Although this invention has been disclosed and illustrated with reference to particular embodiments, the principles involved are susceptible for use in numerous other embodiments which will be apparent to person skilled in the art. The invention is, therefore, to be limited only as indicated by the scope of the appended claims.

We claim:

1. A rotatable cutter for excising obstructive tissue from a lumen of a blood vessel which comprises:
   a hollow cylindrical base;
   a hollow cylindrical tip coaxially distanced from said base and having a diameter less than that of said base;
   a hollow frustum coaxially aligned intermediate and respectively attached to said base and said tip, said frustum formed with a first opening and a second opening to establish a rigid first blade and a rigid second blade, said first and second blades respectively having a first cutting edge and a second cutting edge substantially diametrically opposed to said first cutting edge and wherein said first opening is larger than said second opening to establish said first edge longer than said second edge;
   a guide wire insertable through said base and said tip for guiding said cutter along a predetermined path; and
   means fixedly attached to said base for rotating said cutting edges of said cutter in the same rotational direction to alternately engage said first and second edges with obstructive tissue and establish a differential cutting action between said edges to incline the axis of rotation of said cutter relative to said guide wire.

2. A rotatable cutter as recited in claim 1 wherein said first and second cutting edges are straight.

3. A rotatable cutter as cited in claim 2 wherein said first blade and said second blade are inclined to the longitudinal axis of said cutter at an angle in the range between forty and seventy degrees.

4. A rotatable cutter as cited in claim 3 wherein said cutter is made of stainless steel.

5. A rotatable cutter for excising obstructive tissue from a lumen of a blood vessel which comprises:
   a hollow cylindrical-shaped base;
   a hollow cylindrical-shaped tip coaxially distanced from said base and having a diameter less than that of said base;
   a first rigid blade connecting said base to said tip to establish a first leading cutting edge therebetween;
   a second rigid blade connecting said base to said tip to establish a second leading cutting edge therebetween, said second leading cutting edge being longer than said first leading cutting edge;
   a guide wire insertable through said base and said tip for guiding said cutter along a predetermined path; and
   means fixedly attached to said base for rotating said cutting edges of said cutter in the same rotational direction to alternately engage said first and second edges with obstructive tissue and establish a differential cutting action between said edges to incline the axis of rotation of said cutter relative to said guide wire.

6. A rotatable cutter as cited in claim 5 wherein said first blade and said second blade are substantially straight.

7. A rotatable cutter as cited in claim 6 wherein said first blade and said second blade are each inclined to the common axis of said tip and said base at an angle in the range between forty and seventy degrees.

8. A rotatable cutter as cited in claim 7 wherein said base and said tip are hollow.

9. A rotatable cutter as cited in claim 8 wherein said cutter is made of stainless steel.

10. A rotatable cutter as recited in claim 5 further comprising a motor, and wherein said rotating means is a torque tube having a first end attached to said base and having a second end operatively engaged with said motor.

* * * * *